(12) United States Patent
McNulty et al.

(10) Patent No.: US 8,384,386 B2
(45) Date of Patent: Feb. 26, 2013

(54) DEDICATED SYSTEM FOR MSK JOINT IMAGING

(75) Inventors: Christopher McNulty, Concord, MA (US); Peter B. Roemer, North Andover, MA (US); Robert Stevens, Chelmsford, MA (US); Yuan Cheng, Andover, MA (US)

(73) Assignee: General Electric Company, Schenectady, NY (US)

( * ) Notice: Subject to any disclaimer, the term of this patent is extended or adjusted under 35 U.S.C. 154(b) by 615 days.

(21) Appl. No.: 12/615,385

(22) Filed: Nov. 10, 2009

(65) Prior Publication Data

US 2010/0171500 A1    Jul. 8, 2010

Related U.S. Application Data

(63) Continuation of application No. PCT/US2008/006028, filed on May 12, 2008.

(60) Provisional application No. 60/928,622, filed on May 10, 2007.

(51) Int. Cl.
*G01V 3/00* (2006.01)

(52) U.S. Cl. ......................... 324/318; 324/309

(58) Field of Classification Search .......... 324/300–322; 600/407–445
See application file for complete search history.

(56) References Cited

U.S. PATENT DOCUMENTS

| | | | |
|---|---|---|---|
| 1,092,435 A | 4/1914 | Dorrance | |
| 2,845,543 A | 7/1958 | Hansen et al. | |
| 4,834,112 A | 5/1989 | Machek et al. | |
| 4,875,485 A | 10/1989 | Matsutani | |
| 5,304,930 A | 4/1994 | Crowley et al. | |
| 5,343,580 A | 9/1994 | Bonutti | |
| 5,382,904 A * | 1/1995 | Pissanetzky | 324/319 |
| 5,396,207 A * | 3/1995 | Dorri et al. | 335/216 |
| 5,520,181 A | 5/1996 | Kreidler et al. | |
| 5,541,515 A | 7/1996 | Tsujita | |
| 5,585,724 A * | 12/1996 | Morich et al. | 324/318 |
| 5,646,532 A * | 7/1997 | Knuttel et al. | 324/321 |
| 5,724,970 A | 3/1998 | Votruba et al. | |
| 5,810,006 A | 9/1998 | Votruba et al. | |
| 6,195,578 B1 * | 2/2001 | Distler et al. | 600/415 |
| 6,229,310 B1 * | 5/2001 | Green et al. | 324/318 |
| 6,346,814 B1 | 2/2002 | Carrozzi et al. | |
| 6,377,830 B1 | 4/2002 | Carrozzi et al. | |
| 6,946,836 B2 * | 9/2005 | Kuhara | 324/307 |
| 7,379,769 B2 * | 5/2008 | Piron et al. | 600/415 |
| 2002/0123681 A1 * | 9/2002 | Zuk et al. | 600/410 |
| 2004/0138553 A1 | 7/2004 | Damadian | |
| 2008/0255443 A1 * | 10/2008 | Piron et al. | 600/410 |
| 2010/0102814 A1 * | 4/2010 | Satragno et al. | 324/309 |

FOREIGN PATENT DOCUMENTS

JP          04354934          12/1992

* cited by examiner

Primary Examiner — Brij B Shrivastav

(57) ABSTRACT

A system and method are presented that facilitate imaging of the joints of the upper and lower extremities including, for example, the hip and shoulder as well as sections of the spine, among others. One embodiment of the invention includes a short bore cylindrical magnet with an imaging volume smaller than that of a comparable whole body system, an articulated table that allows placement of the joint to be imaged in the center of the magnet homogeneous volume while maintaining a high degree of patient comfort and openness. The gradient and RF coils may be positioned above and below the patient instead of 360 degrees surrounding the patient. A smaller RF and gradient coil is made feasible because of the reduced imaging volume.

25 Claims, 8 Drawing Sheets

DEDICATED SYSTEM FOR MSK JOINT IMAGING

CROSS-REFERENCE TO RELATED APPLICATIONS

This application is a continuation of and claims priority to International Patent Application No. PCT/US2008/006028, filed May 12, 2008, which in turn claims priority to U.S. Provisional Patent Application Ser. No. 60/928,622, filed May 10, 2007. Each of the aforementioned patent applications is incorporated by reference herein in its entirety.

BACKGROUND OF THE INVENTION

1. Field of the Invention

The present invention relates to a method and system for generating medical images. Particularly, the present invention is directed to a method and system for generating magnetic resonance ("MR") images of a patient.

2. Description of Related Art

A variety of systems and related methods are known in the art for generating magnetic resonance images of a patient. Currently, whole body MRI systems utilize, among other things, cylindrical superconducting magnets to facilitate imaging of the entire human body using linear moving patient tables and magnets with large homogeneous volumes. The inner diameter typically accessible to the patient is from about 600 mm to about 700 mm. The magnets are typically 1.75 to 2.25 meters long. Some systems have magnets as short as 1.25 meters. The typical imaging volume is 350 mm to 450 mm in each of three dimensions with the shorter systems having smaller homogeneous volumes. As known in the art, references herein to such homogeneous volumes refer to regions of sufficient magnetic field uniformity to facilitate creation of useful MRI images.

Some extreme engineering design measures can be taken whereby the amount of superconducting wire in the main magnet is greatly increased in attempts to improve the size of the homogeneous volume at shorter magnet lengths. However, this can only help to a limited extent. The physics and engineering limits require a reduction in homogeneous volume as the magnet is made shorter.

The hip and shoulder joints are off patient center in left/right directions during imaging. The preferred imaging field-of-view for imaging these joints is about 160 mm or less for an imaging volume centered about the joint. However, the magnet's useful imaging volume must be larger to place the desired joint in a good portion of the imaging volume even though the necessary imaging field-of-view is substantially less than the overall imaging volume of the system. An off center imaging sequence is prescribed resulting in an image acquisition centered about the joint.

Along with a large imaging volume in such devices, there is also a requirement to create an RF transmit magnetic field and gradient magnetic field that that spans the entire imaging volume. These coils are generally cylindrical occupying the volume between the magnet and patient bore for a full 360 degrees surrounding the patient.

Such conventional methods and systems generally have been considered satisfactory for their intended purpose. However, such systems are necessarily large. The larger the system, the larger the main magnet needs to be to surround the patient volume, gradient and RF coils. These larger gradient coils, in turn, require more power. Extra space in the facility along with a larger Radio Frequency shielded room is also required. The main magnet is mainly made using low temperature superconductors ("LTS") such as niobium-titanium and the like. These materials are expensive. All of these factors increase the system costs. As such, there is a continuing need in the art for more suitably designed imaging systems that minimize these and other drawbacks. The present invention provides a solution for these and other problems.

SUMMARY OF THE INVENTION

The purpose and advantages of the present invention will be set forth in and become apparent from the description that follows. Additional advantages of the invention will be realized and attained by the methods and systems particularly pointed out in the written description hereof, as well as from the appended drawings.

To achieve these and other advantages and in accordance with the purpose of the invention, as embodied herein, a new and useful system is presented that facilitates imaging of the joints of the upper and lower extremities including, for example, the hip and shoulder as well as sections of the spine. One embodiment of the invention includes a short bore cylindrical magnet with an imaging volume smaller than that of a comparable whole body system, an articulated table that allows placement of the joint to be imaged in the center of the magnet homogeneous volume while maintaining a high degree of patient comfort and openness.

In accordance with a further aspect of the invention, the gradient and RF coils may be positioned above and below the patient instead of 360 degrees surrounding the patient, as in prior art systems. This aspect may allow for a smaller magnet to be used with the same or improved left/right patient aperture. A smaller RF and gradient coil is made feasible because of the reduced imaging volume. The smaller RF coil requires less power for the same performance and reduce RF power deposition (SAR or Specific Absorption Rate) that can cause heating and less dB/dt (time rate of field) that can cause peripheral nerve stimulation.

It is to be understood that both the foregoing general description and the following detailed description are exemplary and are intended to provide further explanation of the invention disclosed herein.

The accompanying drawings, which are incorporated in and constitute part of this specification, are included to illustrate and provide a further understanding of the method and system of the invention. Together with the description, the drawings serve to explain the principles of the invention.

DETAILED DESCRIPTION OF THE PREFERRED EMBODIMENT

Figure 1:
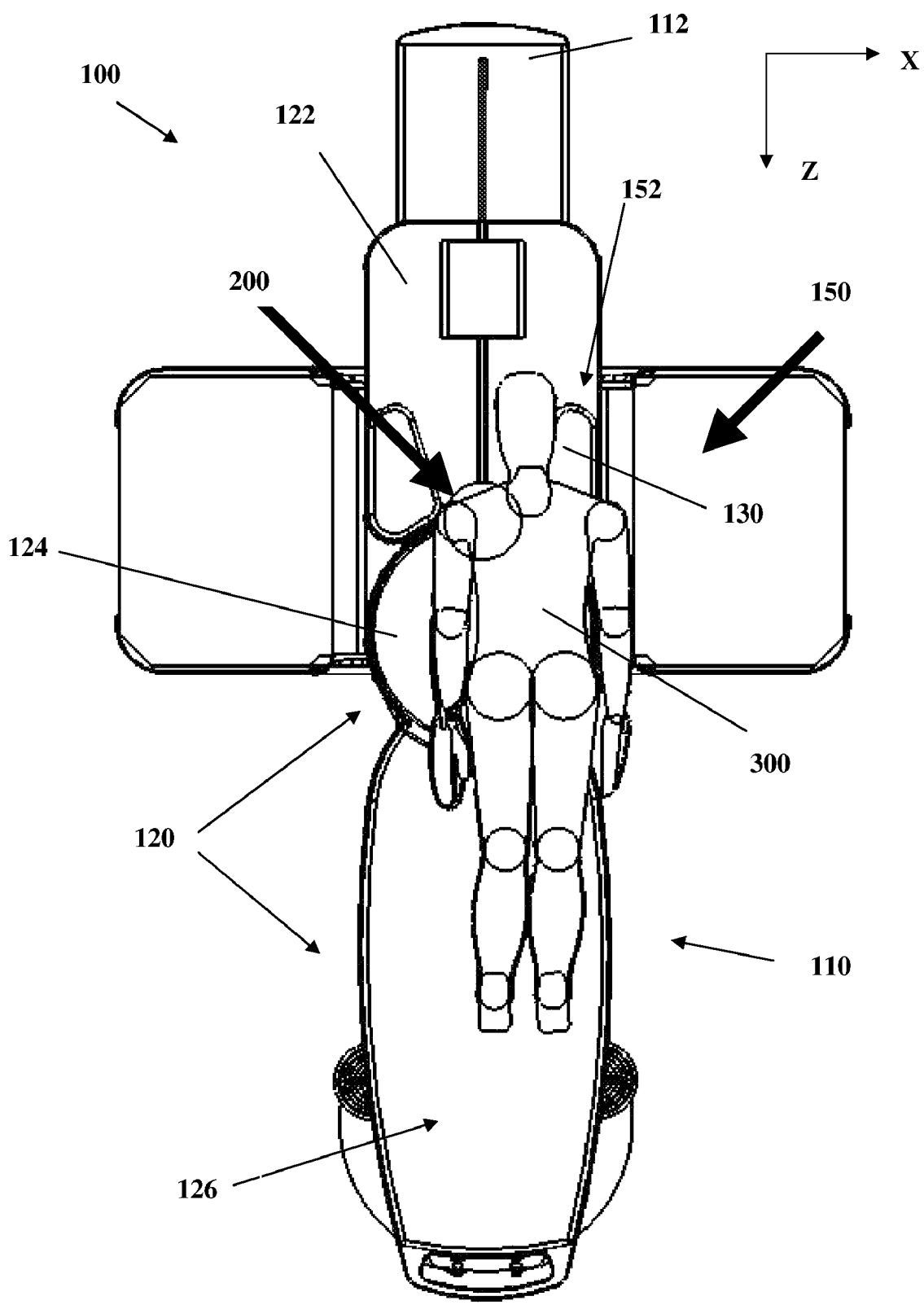
FIG. 1 is a schematic view of a representative embodiment of an imaging device made in accordance with the present invention, illustrating positioning of a patent in a straight orientation with respect to the device.

Reference will now be made in detail to the present preferred embodiments of the invention, examples of which are illustrated in the accompanying drawings. The method and corresponding steps of the invention will be described in conjunction with the detailed description of the system.

The devices and methods presented herein may be used for generating medical images. Particularly, the present invention is directed to a method and system for generating magnetic resonance ("MR") images of a patient.

Embodiments of the invention depicted herein include a combination of magnet and articulated patient table that allow the hip, shoulder, foot, ankle, knee, hand, wrist and elbow joints to be positioned and imaged in a smaller cylindrical MRI magnet. Particular embodiments described herein allow all of the joints of interest of the human body to be centered in the magnet, yet permit use of a magnet with an associated homogenous volume that is substantially smaller than typical systems known in the art. This results in a smaller, lighter, more compact and less costly system that is conveniently more open for the patient.

For purpose of explanation and illustration, and not limitation, views of an exemplary embodiment of an imaging system made in accordance with the invention are shown in FIGS. 1-8 and is designated generally by reference character 100.

As depicted, in FIGS. 1-7, system 100 includes a table 110 operably coupled to a magnet assembly 150 defining a bore 152 therethrough. The magnet assembly 150 can be a conventional design with a cylindrical gradient coil and RF body coil or may be open on the sides as permitted by the teachings of the embodiment illustrated and described herein in further detail below with reference to FIG. 8.

As depicted in FIGS. 1-7, patient table 110 includes a stationary base portion 112 upon which is mounted an articulated portion 120 upon which a patient 300 rests. Articulated portion 120 of table 110 includes a first linear displaceable segment 122, a second generally round pivoting segment 124 and a third angularly displaceable segment 126. The three components of articulated portion 120 of table 110 may be displaced along an axial direction "Z" of the device 100 along a track 114 formed on base portion 112 through bore 152.

Angularly displaceable segment 126 may be angularly displaced, for example, about a pivot point 128 defined in the center of second segment 124. If desired, second segment 124 and third segment 126 may rotate together about pivot point 128.

As depicted, second and third segments 124, 126 are preferably upholstered for the comfort of patient 300. In addition, table 110 is further provided with pads 130 that may be used for supporting various portions of a patient's anatomy while being imaged. Similarly, as depicted, a displaceable RF coil 132 for imaging the elbow or hand is also provided that is adapted and configured to slide along axis "Z" in a track 134.

For purposes of illustration, the device 100 may be used to examine the shoulder joint. The shoulder joint is furthest from the center of the body in the left/right ("X") direction and is the most difficult joint to place in the center in the magnet. In accordance with certain embodiments of the invention, it is desired to place the shoulder of a patient at or near the center of a significantly smaller imaging volume than is typical of a conventional whole body magnet. This allows for a much smaller and lower cost magnet.

Using conventional technology as a starting point, if one starts with a conventional whole body magnet design of 2.5 meters long and 0.9 m inside diameter (not including the gradient and RF body coil) the resultant useful imaging volume is about a 450 mm diameter sphere. If the magnet is reduced in length to <1 meter, the resultant volume is reduced to about 200 mm in diameter. Further shortening the magnet will reduce the useful volume further.

Such a shorter magnet is depicted in the embodiments of FIGS. 1-7. FIG. 1 depicts a top view of a 1 meter long (along the axis Z) magnet with a 200 mm diameter imaging volume 200 and a 700 mm wide patient bore 152. It will be appreciated that the length of the magnet may be modified somewhat without departing from the scope or spirit of the invention. Preferably, the length of the magnet is between about 0.75 meters and about 1.25 meters. More preferably, the magnet is about one meter long. In accordance with another embodiment, the magnet may be less than one meter long.

The patient is a male with height of 172 cm (68") (average is 175 cm) and distance of 154 mm from body center to the center of the shoulder joint. As clearly depicted in FIG. 1, off center imaging of the shoulder is no longer possible because the magnet is too small. Even with a patient bore as large as 700 mm, and an imaging volume of 200 mm diameter, it is not possible to place the shoulder of a person of average size in the magnet center while still laying flat and parallel to the bore axis ("Z" direction).

Figure 2:
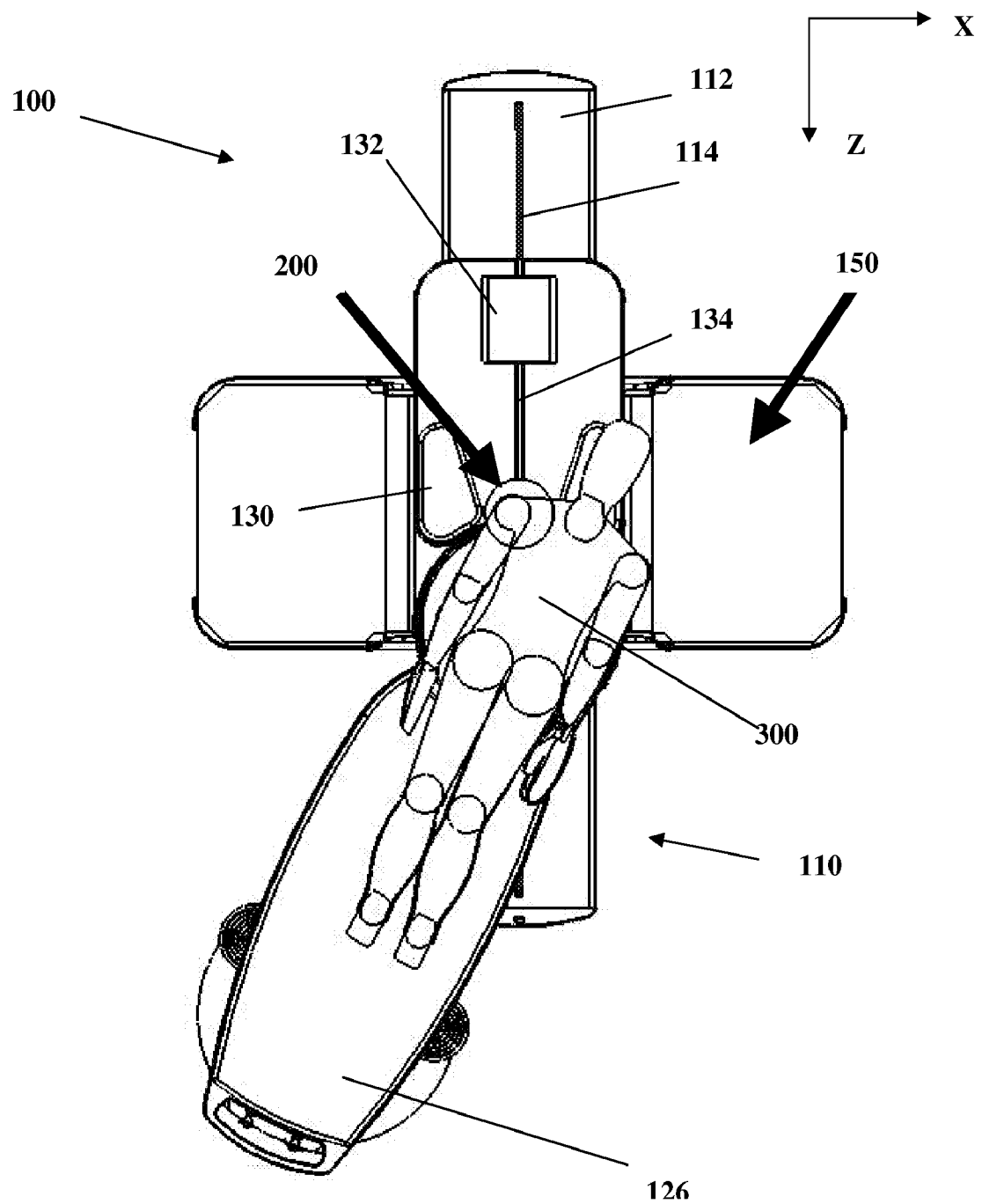
FIG. 2 is a schematic view of the embodiment of FIG. 1 illustrating positioning of a patient in the device to facilitate imaging a shoulder of the patient.

However, by angling portion 126 of the patient table 110 as shown in FIG. 2, the shoulder of patient 300 can now be placed into the center of the imaging volume 200. Angling the patient table is actually facilitated by virtue of the shorter magnet assembly 150. Shorter magnet assembly 150 in turn provides a reduced imaging volume 200. The angled patient table 110 and a relatively short magnet assembly 150 work together to allow the shoulder to be imaged in a smaller, less expensive magnet.

Figure 3:
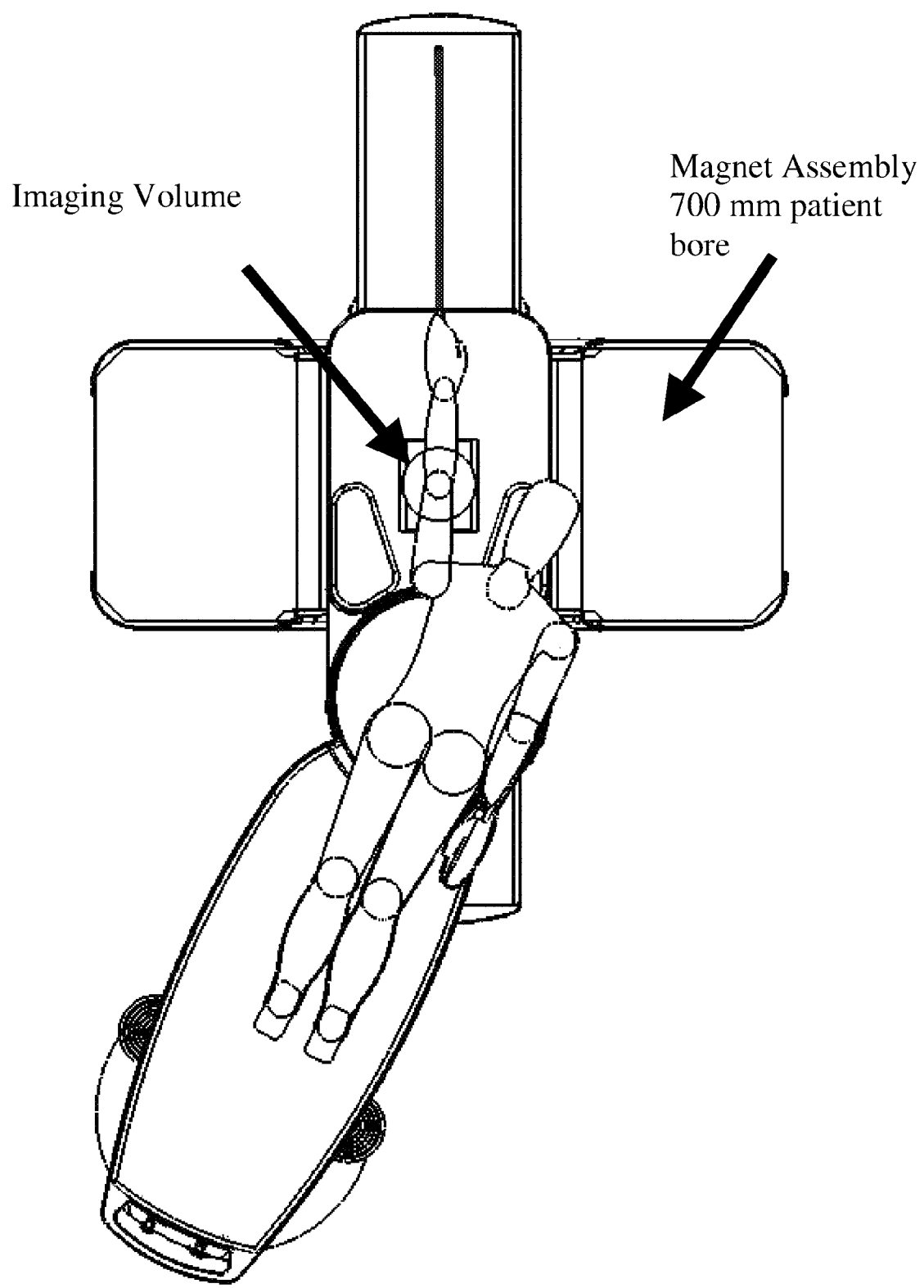
FIG. 3 is a schematic view of the embodiment of FIG. 1 illustrating positioning of a patient in the device to facilitate imaging an elbow of the patient.

Angling the patient table 110 also improves imaging the elbow. As depicted in FIG. 3, the elbow of patient 300 is positioned in the center of the imaging volume 200 and the center of Radio Frequency Coil 132. The patient's arm is not completely extended above the head, which would cause patient discomfort and motion, and the torso is not adjacent to the imaging volume 200, which would otherwise possibly interfere with the image obtained as in the case of a conventional whole body MRI system. Angling the head slightly allows further rotation of portion 126, thereby lowering arm extension resulting in increased patient comfort.

Figure 4:
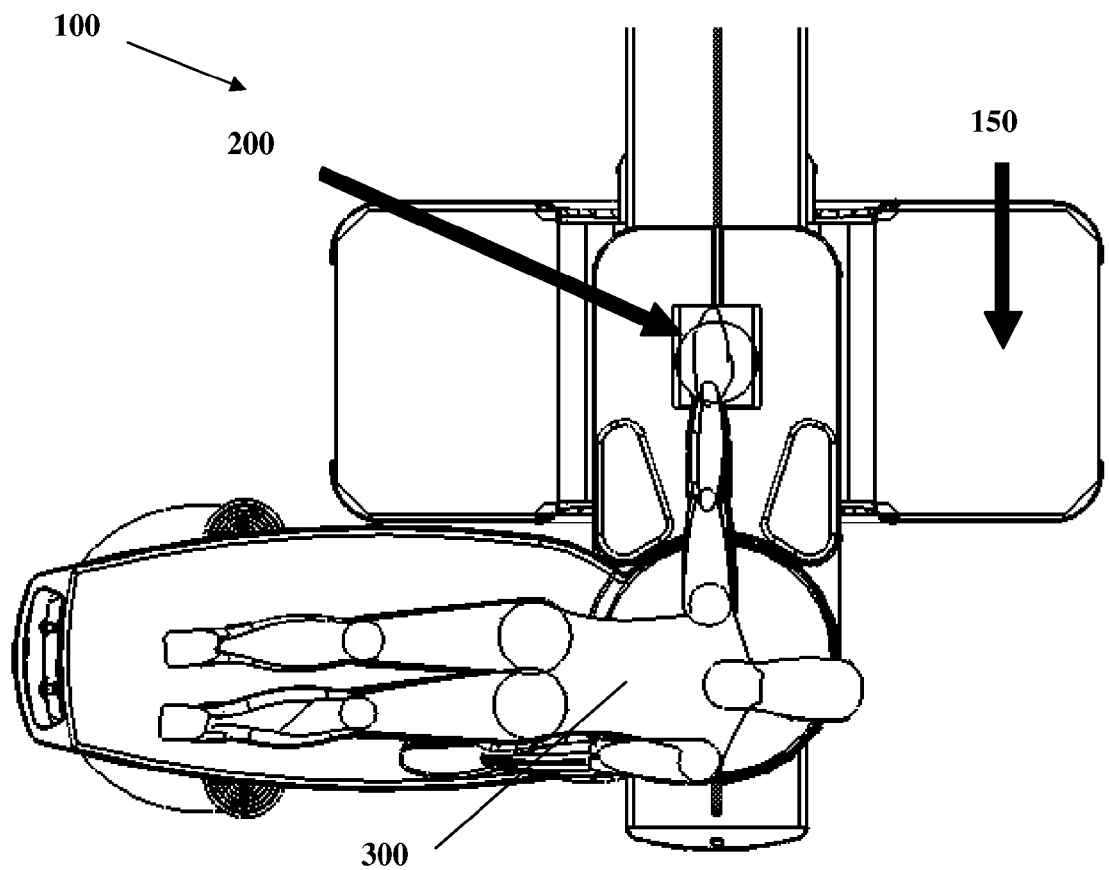
FIG. 4 is a schematic view of the embodiment of FIG. 1 illustrating positioning of a patient in the device to facilitate imaging a hand of the patient.
Figure 5:
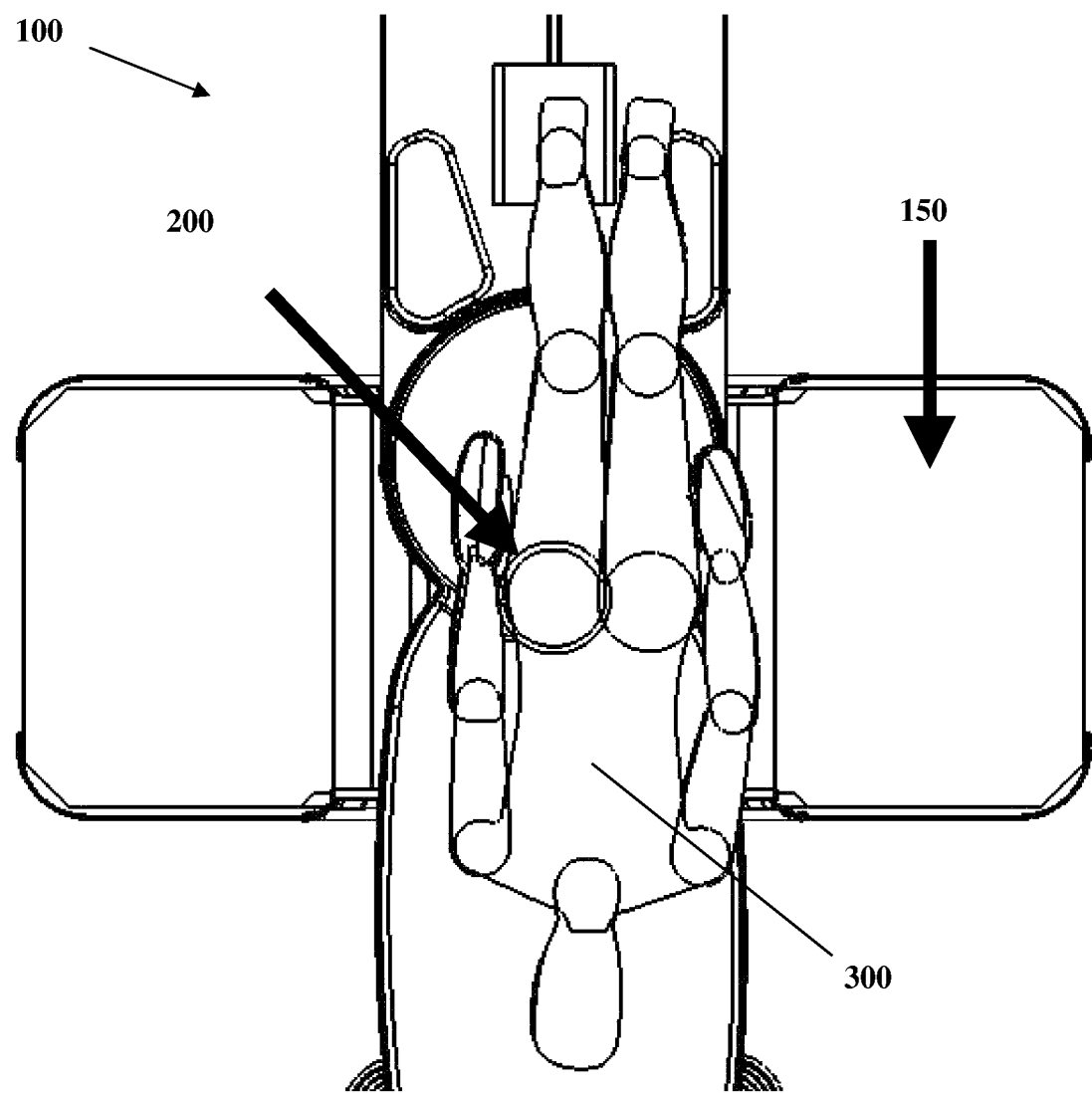
FIG. 5 is a schematic view of the embodiment of FIG. 1 illustrating positioning of a patient in the device to facilitate imaging a hip of the patient.
Figure 6:
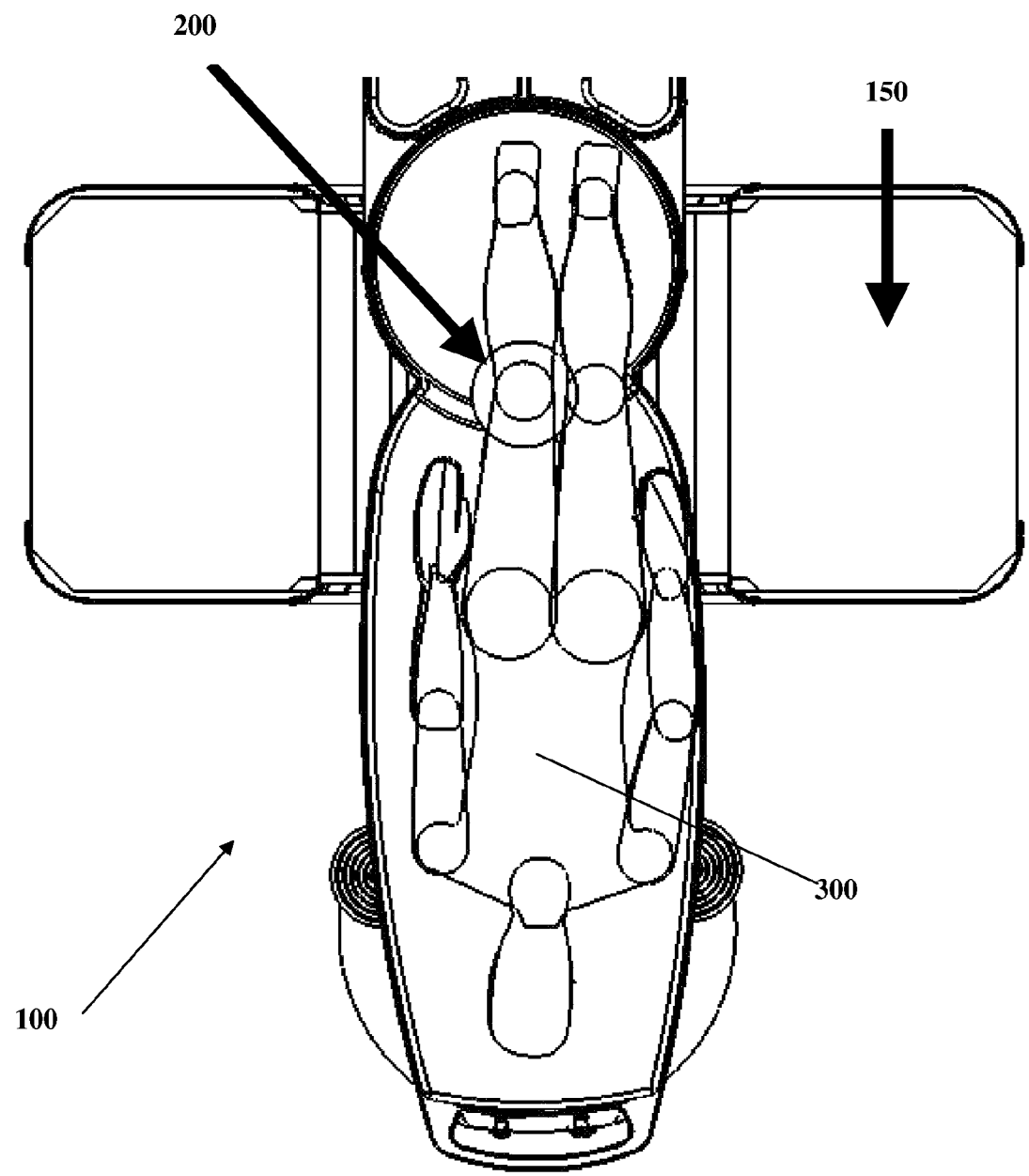
FIG. 6 is a schematic view of the embodiment of FIG. 1 illustrating positioning of a patient in the device to facilitate imaging a knee of the patient.
Figure 7:
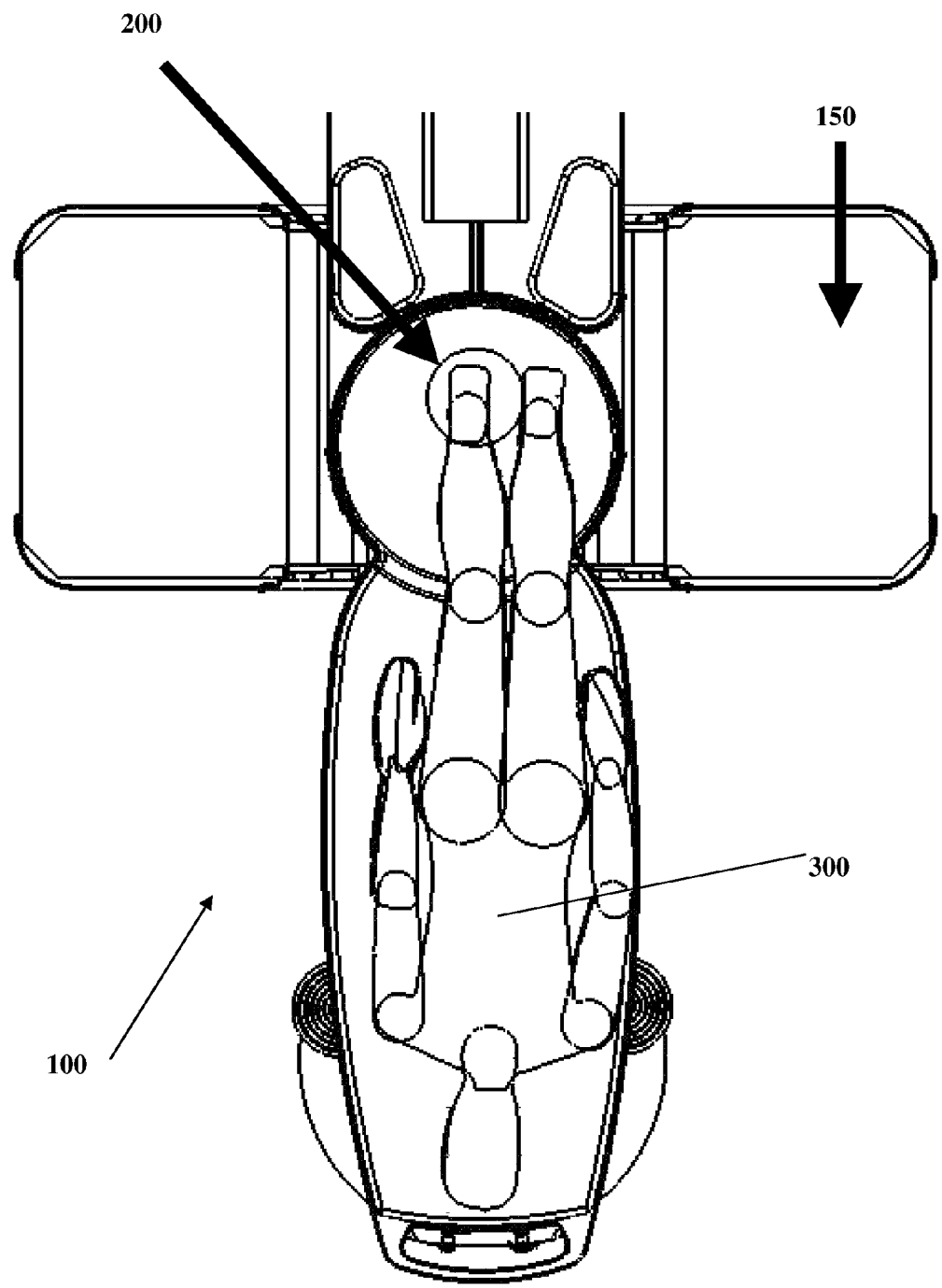
FIG. 7 is a schematic view of the embodiment of FIG. 1 illustrating positioning of a patient in the device to facilitate imaging a foot of the patient.

For imaging the hand of patient 300, the angling of the table 110 is possible with greater patient comfort. As shown in FIG. 4, the hand of patient 300 is in the center of the imaging volume 200, resulting in the highest possible image quality. Similarly, the hip is easily centered in the magnet 150 in a manner that would be similar to a whole body system in FIG. 5. Likewise, the knee joint is easily centered in the magnet 150 in a manner that would be similar to a whole body system in FIG. 6. Furthermore, the ankle joint is easily centered in the magnet assembly 150 in a manner that would be similar to a whole body system in FIG. 7.

The same RF coil 132 has been depicted for imaging the hand, foot, elbow and knee for illustrative purposes only, and not limitation. As known in the art, in practice, different size coils optimized for each anatomical position may be used. The invention described herein is intended to encompass all such embodiments.

Figure 8:
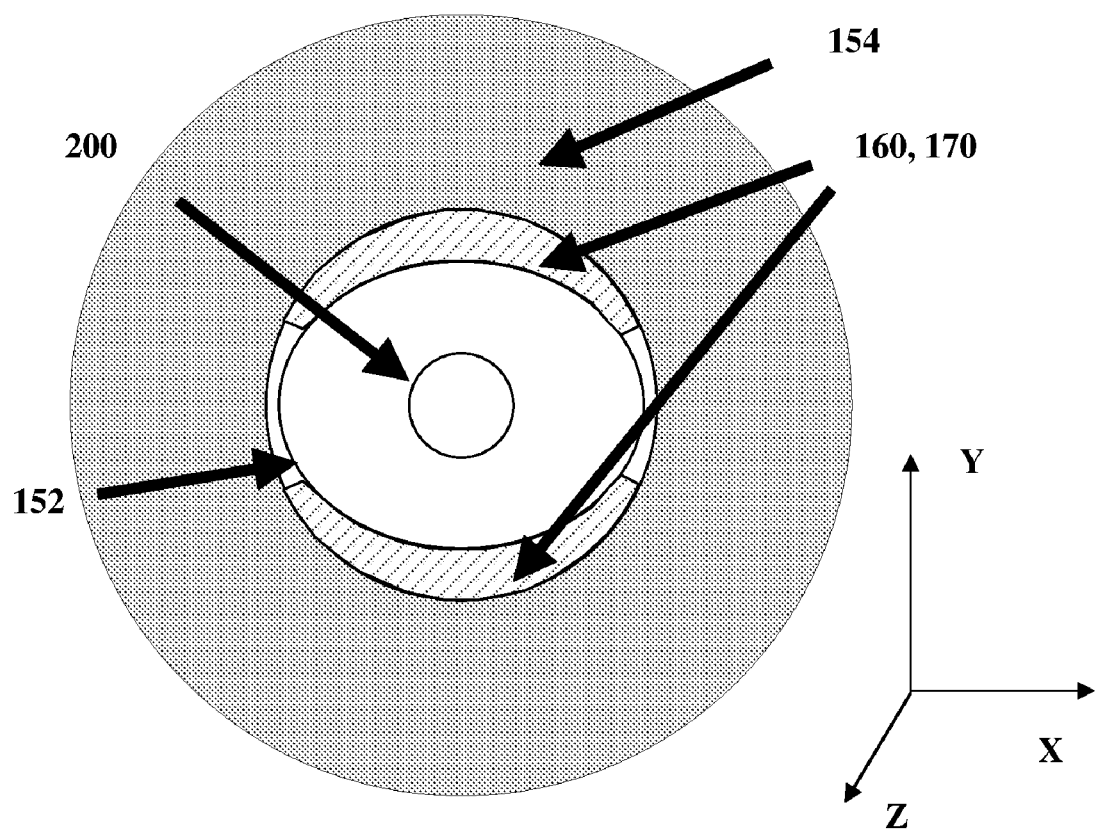
FIG. 8 is a schematic end view of the embodiment of FIG. 1 illustrating placement of the main magnet of the device and gradient and radiofrequency coils.

FIG. 8 presents a schematic end view of the magnet assembly 150 including a main superconducting magnet, 154. As depicted, the imaging volume 200 is about 200 mm in diameter, while the patient bore 152 is about 500 mm in height and about 700 mm in width.

As will be appreciated by those of skill in the art, the size of the imaging volume 200 can be varied in accordance with the size of the magnet assembly 150. For example, the size of the imaging volume can range anywhere from about 50 mm in diameter to about 500 mm in diameter, more preferably from about 100 mm in diameter to about 300 mm in diameter, and most preferably about 200 mm in diameter.

Similarly, the dimensions of the bore can be varied in accordance with the size of the magnet assembly. For example, the width of the bore can vary from about 500 mm to about 1000 mm or larger, more preferably from about 600 mm to about 800, 850 or 900 mm, and most preferably about 700 mm. By way of further example, the height of the bore can vary from about 300 mm to about 1000 mm or larger, more preferably from about 400 mm to about 700 mm, and most preferably about 500 mm.

As depicted in FIG. 8, it is possible to use a smaller RF coil 160 and gradient coil 170 placed above and below the patient instead of a larger set of cylindrical coils surrounding the patient as in a conventional whole body system. This is feasible because of the reduced imaging volume 200 that is needed to perform imaging. Any suitable gradient coil 170 design may be used, as known in the art. The RF coils may include one or more transmit elements that are adapted and configured to transmit signals to a region of interest such as in the imaging volume and receive MR signals from tissue in the region of interest.

The embodiments disclosed herein thus present certain advantages that are heretofore not present in the art. For example, the patient opening can be provided with a larger width by virtue of placement of the RF and gradient coils above and below the patient, instead of surrounding the patient. This, for example, allows for improved access for the shoulder. Moreover, with the RF and gradient coil above and below the patient, the RF transmit uniformity and gradient linearity is feasible for a smaller volume. The gradient amplifier power and RF power required is reduced by virtue of the smaller imaging volume. This allows reduced SAR and dB/dt, which are highly desirable. Perhaps more importantly, the magnet inside diameter can be reduced lowering the cost of the magnet and/or improving homogeneity of the magnetic field while still maintaining access for the shoulder of a patient. A reduced inside diameter of the magnet also permits use a shorter magnet for the same homogeneous volume.

Generally, as the length L of magnet assembly 150 is reduced in length, the homogeneous volume of the magnetic field is necessarily made smaller. The physics of magnetic field generation dictate that the size of the homogeneous volume is reduced in all dimensions even if the magnet is made shorter in just one dimension. However, some limited asymmetric shaping of the homogeneous volume can take place. One example is the oblate spheroid where the equatorial dimension is larger than the polar dimension. In other words, instead of a spherical imaging volume 200, the imaging volume can resemble an ellipsoid that has been compressed along the "Z" dimension in the embodiments depicted in FIGS. 1-7. Such an imaging volume would appear oval from a top view as depicted in FIGS. 1-7, but round in FIG. 8 with the height dimension of the imaging volume in FIGS. 1-7 along the "Z" axis being less than the transverse dimension along the "X" axis and "Y" axis.

It should also be apparent that imaging the head, sections of the spine or any other portion of a patient's anatomy that may be placed in the imaging volume 200 is also possible and straightforward. For example, the spine is near the center of the body which is readily imaged. It will be further appreciated that, while dimensions of magnets and the like are depicted herein, these dimensions are intended to be exemplary and not limiting. It will be further appreciated that system may be operated at any suitable background field produced by main magnet 154. For example, main magnet may adapted to produce a field at 1.0 T, 1.5 T, 2.0 T, 2.5 T, 3.0 T, 4.0 T, 5.0 T, 6.0 T, 7.0 T and the like, as desired. The other portions of system 100 (e.g., coils 160, 170) are accordingly adjusted to accommodate the difference in main field strength.

As can be seen, the methods and systems of the present invention, as described above and shown in the drawings, provide for an imaging system with superior qualities as compared to prior art systems. It will be apparent to those skilled in the art that various modifications and variations can be made in the device and method of the present invention without departing from the spirit or scope of the invention. Thus, it is intended that the present invention include modifications and variations that are within the scope of the subject disclosure and equivalents.

What is claimed is:

1. A magnetic resonance imaging system, comprising:
   a) a magnet assembly defining a generally cylindrical bore for receiving a patient therethrough, the generally cylindrical bore being aligned along a first axis;
   b) a patient table operably coupled to the magnet assembly and adapted and configured to translate along the first axis, the table including:
      i) a first portion adapted and configured to be received by the bore; and
      ii) a second portion that may be angularly displaced with respect to the first axis in a horizontal plane.

2. The system of claim 1, wherein the magnet assembly is adapted and configured to generate a homogeneous volume within the bore that is non-spherical.

3. The system of claim 2, wherein the homogeneous volume is generally shaped as an oblate spheroid, the spheroid having a shorter dimension along the first axis than a second axis transverse to the first axis.

4. The system of claim 1, wherein the magnet assembly includes a radio frequency coil assembly having:
   a) a first radio frequency coil disposed above the bore; and
   b) a second radio frequency coil disposed below the bore.

5. The system of claim 1, wherein the magnet assembly includes a gradient coil assembly having:
   a) a first gradient coil disposed above the bore; and
   b) a second gradient coil disposed below the bore.

6. The system of claim 1, wherein the magnet assembly has a length along the first axis between about 0.75 meters and about 1.25 meters.

7. The system of claim 6, wherein the magnet assembly has a length along the first axis of about one meter.

8. The system of claim 1, wherein the magnet assembly has a length along the first axis that is less than about one meter.

9. The system of claim 1, wherein the bore has a non-circular cross-section along the first axis.

10. The system of claim 1, wherein the bore has a horizontal width between about 600 mm and about 1000 mm.

11. The system of claim 10, wherein the bore has a horizontal width of about 700 mm.

12. The system of claim 1, wherein the bore has a vertical height between about 400 mm and about 1000 mm.

13. The system of claim 12, wherein the bore has a vertical height of about 500 mm.

14. The system of claim 1, further comprising a local radio frequency coil disposed on the patient table.

15. The system of claim 1, wherein the magnet assembly is adapted and configured to generate a main magnetic field along the first axis between about 1.0 Tesla and about 3.0 Tesla.

16. The system of claim 1, wherein the magnet assembly is adapted and configured to generate a homogeneous volume within the bore having an average dimension between about 100 mm and about 300 mm.

17. The system of claim 1, wherein the magnet assembly is adapted and configured to generate a homogeneous volume within the bore having an average dimension of about 200 mm.

18. The system of claim 1, wherein the patient table is adapted and configured to position the shoulder of a patient disposed on the table into a homogeneous volume disposed along the first axis within the bore.

19. The system of claim 1, wherein the patient table is adapted and configured to position the hip of a patient disposed on the table into a homogeneous volume disposed along the first axis within the bore.

20. The system of claim 1, wherein the patient table is adapted and configured to position the knee, wrist or elbow of a patient disposed on the table into a homogeneous volume disposed along the first axis within the bore.

21. A method of performing magnetic resonance imaging, comprising:
   a) providing a magnetic resonance imaging system including:
      i) a magnet assembly defining a generally cylindrical bore for receiving a patient therethrough, the generally cylindrical bore being aligned along a first axis;
      ii) a patient table operably coupled to the magnet assembly and adapted and configured to translate along the first axis, the table including:
         (1) a first portion adapted and configured to be received by the bore; and
         (2) a second portion that may be angularly displaced with respect to the first axis in a horizontal plane; and
   b) disposing a patient on the patient table; and
   c) angulating the patient table with respect to the first axis along the horizontal plane and disposing a portion of the patient to be imaged into a homogenous volume generated by the magnet assembly.

22. The method of claim 21, wherein the patient's shoulder, hip, knee, wrist or elbow is disposed in the homogeneous volume.

23. The method of claim 21, wherein the patient's head or portion of the patient's spine is disposed in the homogeneous volume.

24. The method of claim 21, further comprising performing a magnetic resonance imaging scan of the patient.

25. The method of claim 24, further comprising forming a magnetic resonance image.

* * * * *